United States Patent
Swoyer et al.

(10) Patent No.: US 7,066,935 B2
(45) Date of Patent: Jun. 27, 2006

(54) ION ELUTING TUNA DEVICE

(75) Inventors: John M. Swoyer, Andover, MN (US); Yelena G. Tropsha, Plymouth, MN (US); Julie M. Woessner, St. Paul, MN (US); Mark A. Christopherson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 48 days.

(21) Appl. No.: 10/836,467

(22) Filed: Apr. 30, 2004

(65) Prior Publication Data
US 2005/0245924 A1    Nov. 3, 2005

(51) Int. Cl.
*A61B 18/18* (2006.01)
(52) U.S. Cl. ............................ 606/41; 606/48; 606/49; 606/50; 607/98; 607/99; 607/101; 607/102
(58) Field of Classification Search ................. 606/41, 606/48–50; 607/98–99, 101–102
See application file for complete search history.

(56) References Cited

U.S. PATENT DOCUMENTS

| | | | |
|---|---|---|---|
| 4,391,278 A * | 7/1983 | Cahalan et al. ............ 600/391 |
| 4,554,924 A * | 11/1985 | Engel ........................ 600/391 |
| 5,229,172 A | 7/1993 | Calahan |
| 5,472,441 A * | 12/1995 | Edwards et al. ............. 606/41 |
| 5,542,915 A | 8/1996 | Edwards |
| 5,549,644 A | 8/1996 | Lundquist et al. |
| 5,591,227 A | 1/1997 | Dinh |
| 5,609,629 A | 3/1997 | Fearnot |
| 5,667,488 A | 9/1997 | Lundquist et al. |
| 5,762,626 A | 6/1998 | Lundquist et al. |
| 5,807,309 A | 9/1998 | Lundquist et al. |
| 5,849,011 A | 12/1998 | Jones |
| 5,871,531 A * | 2/1999 | Struble ....................... 607/126 |
| 5,873,877 A | 2/1999 | Mc Gaffigan |
| 5,964,756 A | 10/1999 | McGaffigan |
| 5,997,532 A * | 12/1999 | McLaughlin et al. ........ 606/41 |
| 6,006,139 A * | 12/1999 | Kruse et al. ................ 607/125 |
| 6,071,279 A * | 6/2000 | Whayne et al. .............. 606/41 |
| 6,139,547 A * | 10/2000 | Lontine et al. .............. 606/41 |
| 6,193,714 B1 | 2/2001 | McGaffigan |
| 6,238,393 B1 | 5/2001 | Mulier |
| 6,241,702 B1 | 6/2001 | Lundquist |
| 6,302,903 B1 | 10/2001 | Mulier |
| 6,315,777 B1 | 11/2001 | Comben |
| 6,409,722 B1 | 6/2002 | Hoey |
| 6,494,902 B1 | 12/2002 | Hoey |
| 6,497,705 B1 | 12/2002 | Comben |
| 6,514,247 B1 | 2/2003 | McGaffigan |
| 6,537,248 B1 | 3/2003 | Mulier |

(Continued)

FOREIGN PATENT DOCUMENTS

WO    WO2003005918    1/2003

(Continued)

*Primary Examiner*—Linda C. M. Dvorak
*Assistant Examiner*—Alex Toy
(74) *Attorney, Agent, or Firm*—Anna M. Nelson; Keith M. Campbell

(57) ABSTRACT

Delivery elements, including needle electrodes and sheaths of tissue ablation devices, containing a conductivity-enhancing agent are discussed. The delivery elements contain a body member and optionally one or more coating layers. The conductivity-enhancing agent is disposed on or in the body member and/or at least one of the one or more coating layers. The conductivity-enhancing agent is capable of eluting from the delivery element when the delivery element is contacted with bodily tissue or fluid and increases conductivity of the tissue, making tissue ablation more efficient.

39 Claims, 9 Drawing Sheets

U.S. PATENT DOCUMENTS

| | | |
|---|---|---|
| 6,537,272 B1 | 3/2003 | Christopherson |
| 6,547,787 B1 * | 4/2003 | Altman et al. ............... 606/41 |
| 6,551,300 B1 | 4/2003 | McGaffigan |
| 6,607,529 B1 | 8/2003 | Jones |
| 6,623,515 B1 | 9/2003 | Mulier |
| 2001/0025178 A1 | 9/2001 | Mulier |
| 2001/0041921 A1 | 11/2001 | Mulier |
| 2002/0019628 A1 | 2/2002 | Comben |
| 2002/0026187 A1 * | 2/2002 | Swanson .................... 606/41 |
| 2002/0035387 A1 | 3/2002 | Mulier |
| 2002/0049439 A1 | 4/2002 | Mulier |
| 2002/0058933 A1 | 5/2002 | Christopherson |
| 2002/0058935 A1 | 5/2002 | Hoey |
| 2002/0138123 A1 * | 9/2002 | Casas-Bejar et al. ....... 607/120 |
| 2002/0151884 A1 | 10/2002 | Hoey |
| 2002/0183733 A1 | 12/2002 | Mulier |
| 2003/0073989 A1 | 4/2003 | Hoey |
| 2004/0015160 A1 | 1/2004 | Lovewell |
| 2004/0015161 A1 | 1/2004 | Lovewell |
| 2004/0015162 A1 | 1/2004 | McGaffigan |

FOREIGN PATENT DOCUMENTS

| | | |
|---|---|---|
| WO | WO2003047446 | 6/2003 |
| WO | WO2003092785 | 11/2003 |
| WO | WO2004026361 | 4/2004 |

* cited by examiner

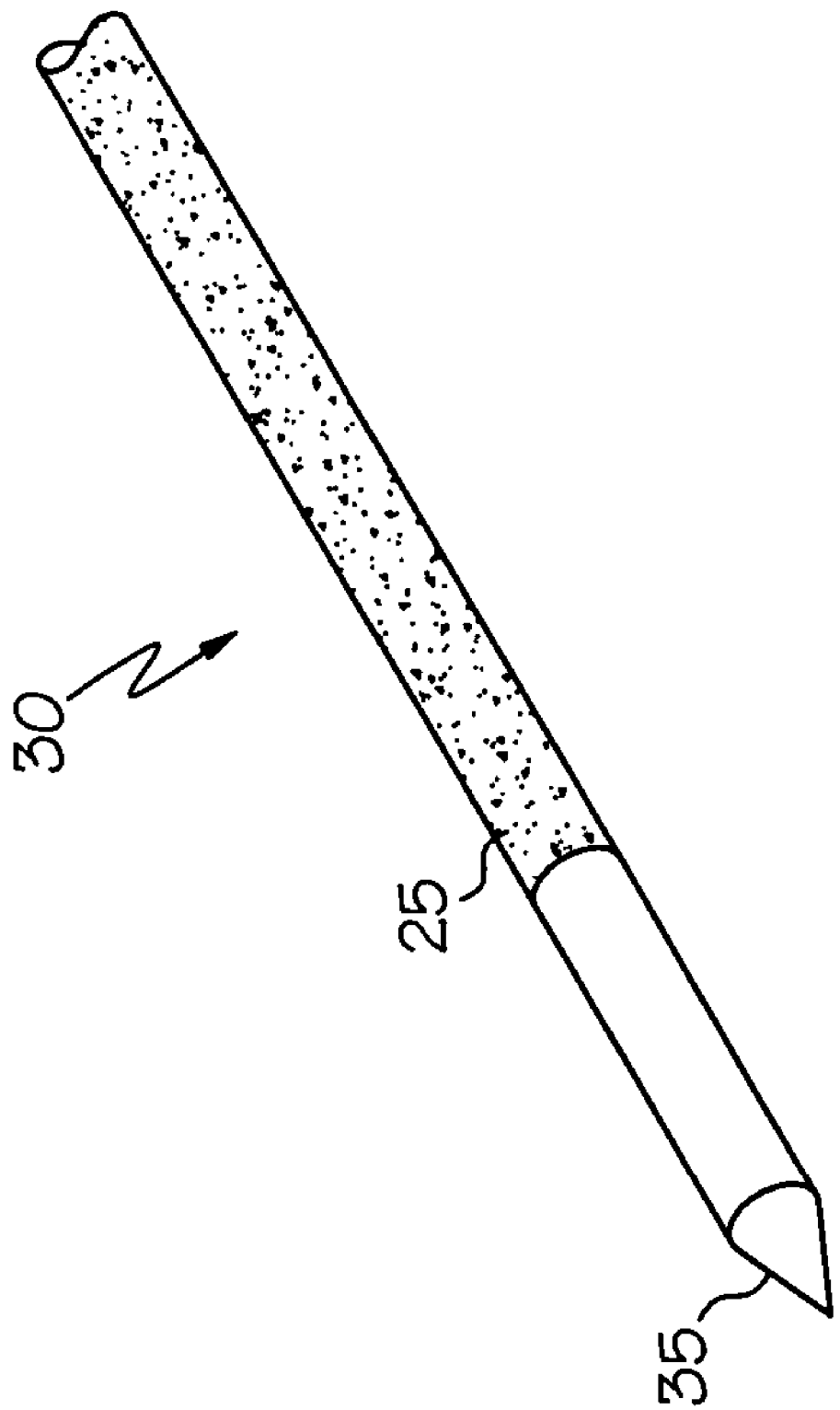

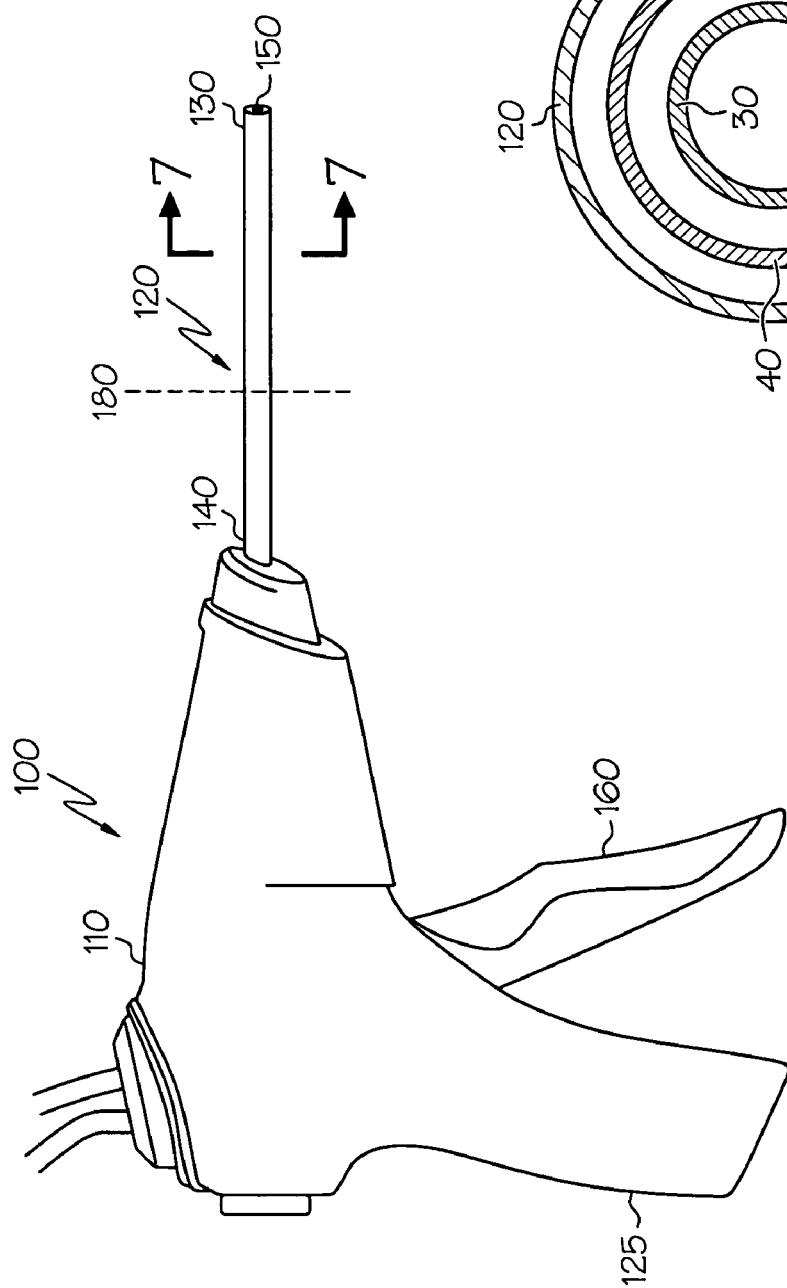
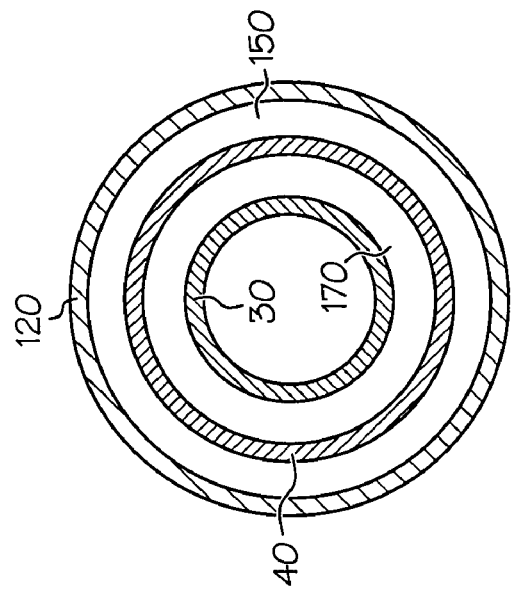
FIG. 7
FIG. 6

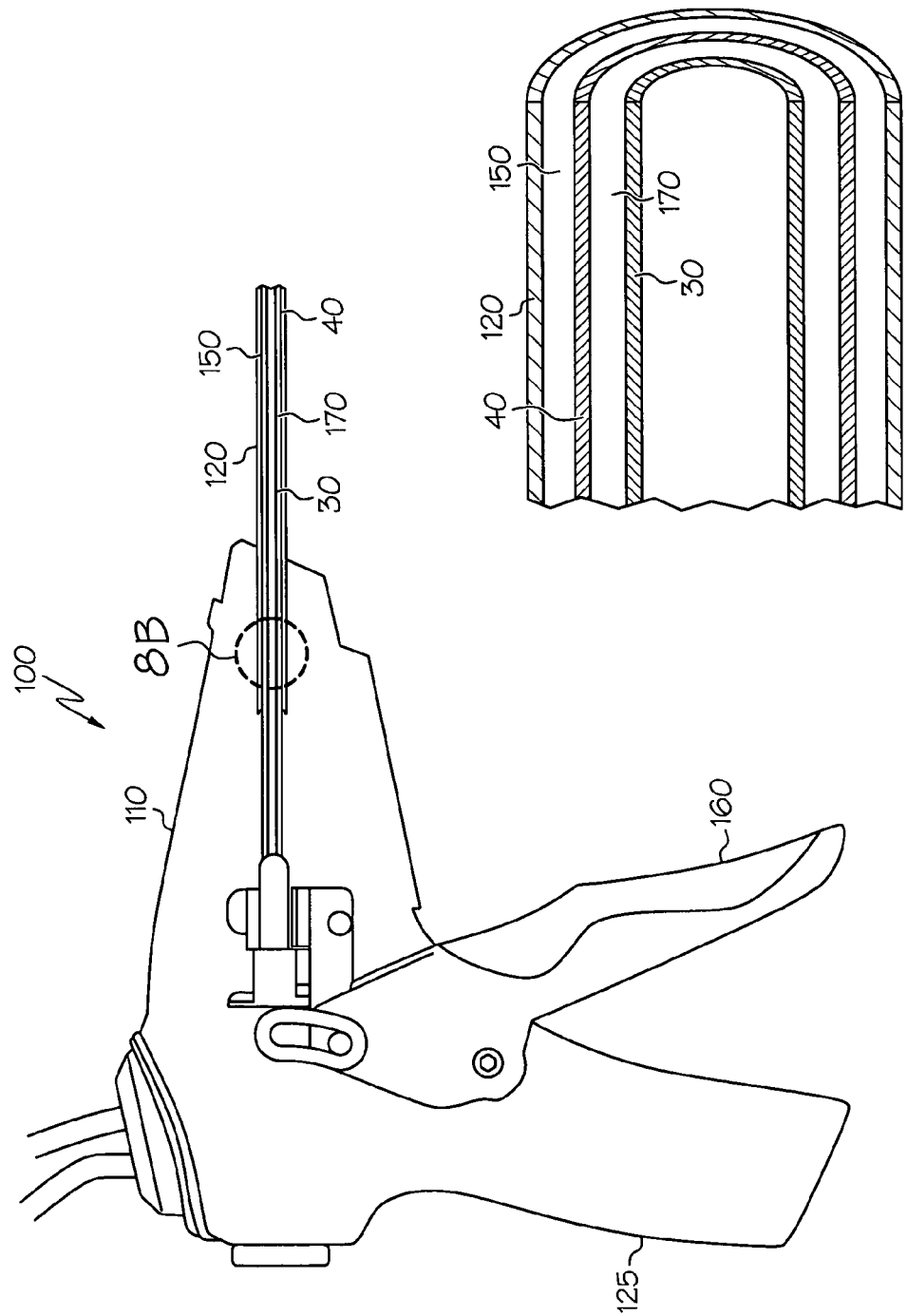

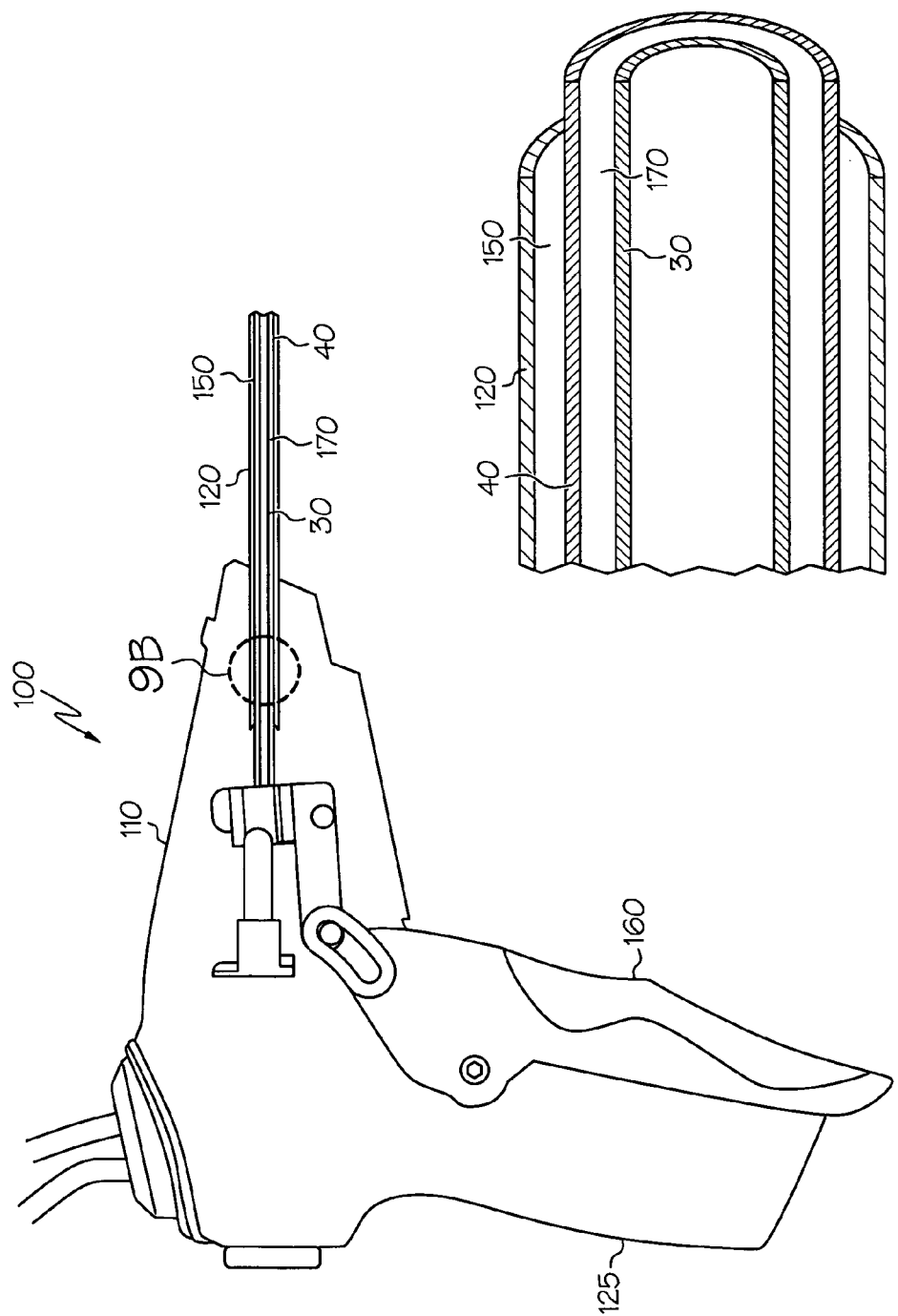

ION ELUTING TUNA DEVICE

FIELD OF THE INVENTION

This invention relates to medical methods and devices and, more particularly, to virtual electrode technology for use in ablating tissue.

BACKGROUND OF THE INVENTION

It has been demonstrated that RF ablation of prostate tissue can be done more efficiently by delivering a conductive solution, such as saline, to the target tissue during the creation of a lesion. The addition of the conductive solution creates a "virtual" electrode larger than the actual electrode, allowing more efficient delivery of RF energy. However, current and proposed virtual electrode systems may prove to be cumbersome and may require additional controls and equipment, making virtual electrode techniques more complex to perform than traditional dry electrode techniques. For example, introduction of conductive fluid and the controls associated with the introduction of the fluid complicate ablation procedures. The present invention provides useful alternatives to existing virtual electrode technology.

BRIEF SUMMARY OF THE INVENTION

In an embodiment, the invention provides a delivery element comprising a conductivity-enhancing agent, such as a salt, capable of increasing conductivity of the tissue when dissolved in the tissue. The delivery element comprises a body member and may comprise one or more coating layers. The conductivity-enhancing agent is disposed on or in at least a portion of the body member and/or at least one of the one or more coating layers. The delivery element may be a needle electrode or a sheath of a tissue ablation device.

An embodiment of the invention provides a device for ablating tissue at a target location. The device comprises a needle electrode having distal and proximal portions. The device further comprises a delivery element, as described above, having a proximal portion and a distal portion. The device further comprises a housing and an elongate probe member extending from the housing. The elongate probe member comprises one or more passageways extending at least substantially from a proximal portion of the probe member to a distal portion of the probe member. The needle electrode and delivery member are slidably disposed in one or two of the at least one or more passageways of the elongate probe member. The device further comprises an actuator, which is coupled to a proximal portion of the needle electrode and is adapted to cause a distal portion of the needle electrode to extend into the target location. The actuator is also coupled to the proximal portion of the delivery element and is adapted to cause the distal portion of the delivery element to extend into the target location. The device may further comprise a sheath comprising a lumen and slidably disposed within the passageway in which the needle is disposed. The sheath is coupled to the actuator, which is adapted to cause at least a portion of the sheath to extend into the target location. The delivery element may be one or more of the needle electrode, the sheath, or a separate element.

An embodiment of the invention provides a method for ablating tissue at a target location. The method comprises introducing into the target location a delivery element comprising a conductivity-enhancing agent. The conductivity-enhancing agent is capable of increasing conductivity of the tissue when dissolved in the target location. The method further comprises introducing an electrode into the target location and ablating the tissue by applying energy to the target location via the electrode. The electrode may be the delivery element. A sub-ablation amount of energy may be applied to the electrode to drive the salt from the element into the tissue prior to applying sufficient energy to ablate the tissue.

The present invention provides several advantages over existing technology. For example, embodiments of the invention eliminate the need for addition steps to deliver a fluid to achieve the benefits of a virtual electrode. By disposing a polymer comprising a conductive salt on, e.g., a needle or a sheath of a tissue ablation device, the need for introducing a conductive fluid is eliminated because the salt may diffuse out of the polymer when the sheath or needle is introduced to a location containing the tissue to be ablated. Further, additional equipment needed for the delivery of a conductive fluid, such as a pump, may be eliminated. These and other advantages will become evident upon reading the disclosure presented herein.

BRIEF DESCRIPTION OF THE DRAWINGS

FIG. 5 is a diagrammatic representation of a porous sheath disposed over a needle electrode according to an embodiment of the invention.

FIG. 6 is a diagrammatic representation of an exterior view of a tissue ablation device according to an embodiment of the invention.

FIG. 7 is a diagrammatic representation of a cross section of the device in FIG. 6.

FIGS. 8a and 8b are diagrammatic representations of longitudinal sections of a portion of the device shown in FIG. 6, illustrating an embodiment of the invention.

FIGS. 9a and 9b are diagrammatic representations of longitudinal sections of a portion of the device shown in FIG. 6, illustrating an embodiment of the invention.

The drawings are not necessarily to scale. Like numbers refer to like parts or steps throughout the drawings.

DETAILED DESCRIPTION OF THE INVENTION

Figure 1A:
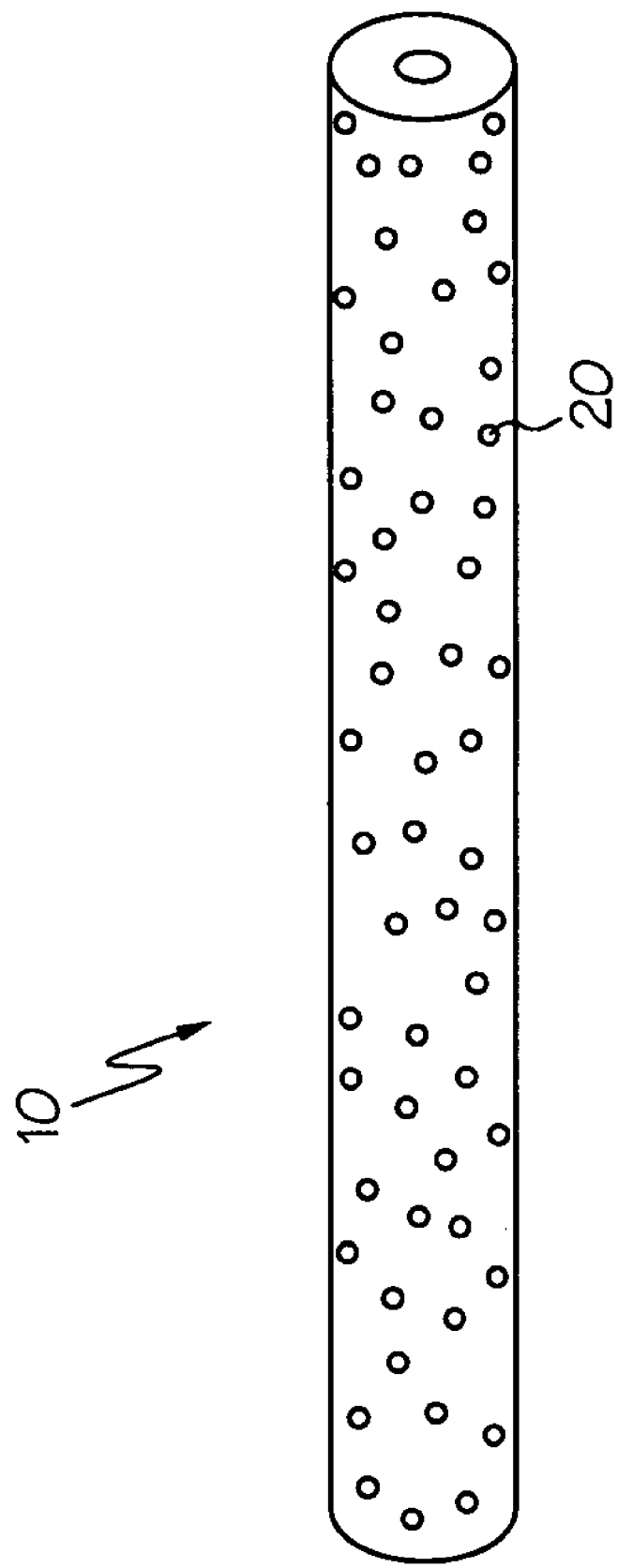
FIGS. 1A–1E are diagrammatic illustrations of a perspective view (A) and cross sections (B–F) of delivery elements comprising associated conductivity-enhancing agent according to various embodiments of the invention.

In the following description, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense. Instead, the scope of the present invention is to be defined in accordance with the appended claims.

The present invention, in various embodiments, relates to methods, apparatuses, and systems employing virtual electrode technology. In various embodiments, the virtual electrode technology may be applied to trans-urethral needle ablation TUNA procedures, devices and systems. Various patents and patent applications that discuss virtual electrode technology and TUNA include:

US 20030073989, Apparatus and method for creating, maintaining, and controlling a virtual electrode used for the ablation of tissue
U.S. Pat. No. 6623515, Straight needle apparatus for creating a virtual electrode used for the ablation of tissue
U.S. Pat. No. 6537272, Apparatus and method for creating, maintaining, and controlling a virtual electrode used for the ablation of tissue
U.S. Pat. No. 6537248, Helical needle apparatus for creating a virtual electrode used for the ablation of tissue
US 20020183733, HELICAL NEEDLE APPARATUS FOR CREATING A VIRUTAL ELECTRODE USED FOR THE ABLATION OF TISSUE
US 20020151884, Apparatus and method for creating, maintaining, and controlling a virtual electrode used for the ablation of tissue
U.S. Pat. No. 6497705, Method and apparatus for creating a virtual electrode used for the ablation of tissue
U.S. Pat. No. 6494902, Method for creating a virtual electrode for the ablation of tissue and for selected protection of tissue during an ablation
U.S. Pat. No. 6409722, Apparatus and method for creating, maintaining, and controlling a virtual electrode used for the ablation of tissue
US 20020058935, METHOD FOR CREATING A VIRTUAL ELECTRODE FOR THE ABLATION OF TISSUE AND FOR SELECTED PROTECTION OF TISSUE DURING AN ABLATION
US 20020058933, Apparatus and method for creating, maintaining, and controlling a virtual electrode used for the ablation of tissue
US 20020049439, Helical needle apparatus for creating a virtual electrode used for the ablation of tissue
US 20020035387, Straight needle apparatus for creating a virtual electrode used for the ablation of tissue
US 20020019628, Method and apparatus for creating a virtual electrode used for the ablation of tissue
U.S. Pat. No. 6315777, Method and apparatus for creating a virtual electrode used for the ablation of tissue
U.S. Pat. No. 6302903, Straight needle apparatus for creating a virtual electrode used for the ablation of tissue
US 20010041921, STRAIGHT NEEDLE APPARATUS FOR CREATING A VIRTUAL ELECTRODE USED FOR THE ABLATION OF TISSUE
US 20010025178, Method and apparatus for creating a bi-polar virtual electrode used for the ablation of tissue
U.S. Pat. No. 6238393, Method and apparatus for creating a bi-polar virtual electrode used for the ablation of tissue
WO 2003047446, FEEDBACK SYSTEM FOR RF ABLATION BY MEANS OF A VIRTUAL ELECTRODE AND COOLING PROTECTION, METHOD THEREFOR
WO 2003005918, APPARATUS AND METHOD FOR CREATING, MAINTAINING, AND CONTROLLING A VIRTUAL ELECTRODE USED FOR THE ABLATION OF TISSUE All printed publications, such as patents, patent applications, technical papers, and brochures, cited herein are hereby incorporated by reference herein, each in its respective entirety. As those of ordinary skill in the art will readily appreciate upon reading the description herein, at least some of the devices and methods disclosed in the patents and publications cited herein may be modified advantageously in accordance with the teachings of the present invention.

The present invention relates to tissue ablation employing virtual electrode technology. In various embodiments the invention provides methods, systems and devices useful for such technology. In particular embodiments, the invention provides a delivery element adapted for use in a tissue ablation device. The delivery element comprises a body member and optionally one or more coating layers. The body member and/or the one or more coating layers comprise one or more conductivity-enhancing agents that may be eluted from the delivery element when the delivery element is contacted with bodily fluid or tissue. The delivery element may take the form of, e.g., a needle electrode or an insulating sheath of a tissue ablation device. Introducing the sheath or needle into a tissue, a step typically employed in tissue ablation procedures, allows for the release of the conductivity enhancing agent(s) into the tissue, increasing the conductivity of the tissue. The increased tissue conductivity may create a virtual electrode larger than the actual electrode, such as a needle electrode, increase the efficiency with which tissue may be ablated, and allow for more efficient delivery of energy, such as RF energy. By incorporating the conductivity-enhancing agent on a delivery element, various embodiments of the invention eliminate the need for addition steps and equipment to deliver a fluid to achieve the benefits of a virtual electrode.

Conductivity Enhancing Agent

Referring to FIG. 1, an embodiment of the invention provides a conductivity-enhancing agent 20 associated with a delivery element 10. The delivery element 10 may be a component, such as a needle electrode 30 or a sheath 40, of a tissue ablation device 100 as shown in, e.g., FIGS. 6–9. Conductivity enhancing agent 20 may be associated with a delivery element 10 in any fashion such that contacting at least a portion of the delivery element 10 with a tissue of a subject allows for the conductivity-enhancing agent to dissolve or elute into the tissue.

As used herein, "conductivity-enhancing agent" 20 means an agent capable of increasing electrical conductivity of a tissue in which the agent 20 is placed and is capable of producing ions when placed in contact with an aqueous environment, such as a tissue of a subject. A conductivity-enhancing agent 20 may produce any ion capable of enhancing the conductivity of an environment to which the ion is introduced. For example, a conductivity-enhancing agent 20 may produce a cation having a charge of, e.g., +1 to +3 and may produce an anion having a charge of, e.g., −1 to −3. A conductivity-enhancing agent 20 may be a salt. Any medically acceptable salt may be employed according to various embodiments of the invention. By way of example, a conductivity enhancing salt may comprise sodium, potassium, calcium, and/or magnesium as the potential cation and may contain chloride, nitrate, nitrite, sulfate, phosphate, sulfate, and/or carbonate as the potential anion. The salts may be monobasic, dibasic, tribasic, etc. Specific exemplary salts include $NaCl$, $CaCl_2$, $MgCl_3$, $KMgCl_3$, $Na_2SO_3$, $CaSO_4$, $MgSO_4$, $Na_2HPO_4$, $Ca_{10}(PO_4)_6$, $Mg_3(PO_4)_2$, $NaHCO_3$, $CaCO_3$, $MgCO_3$, $CaMgCO_3$, $NaNO_3$, $NaNO_2$, $KCl$, $KNO_3$, and $KNO_2$. Reference to a salt herein is intended to refer to anhydrous and hydrated forms of the salt.

Figure 1C:
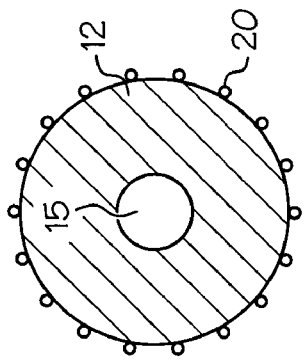
Figure 1E:
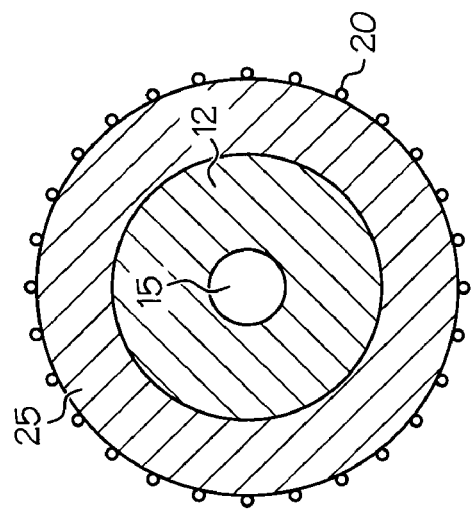
Figure 1B:
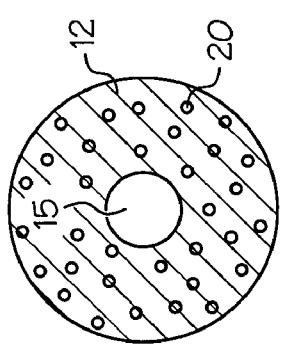
Figure 1D:
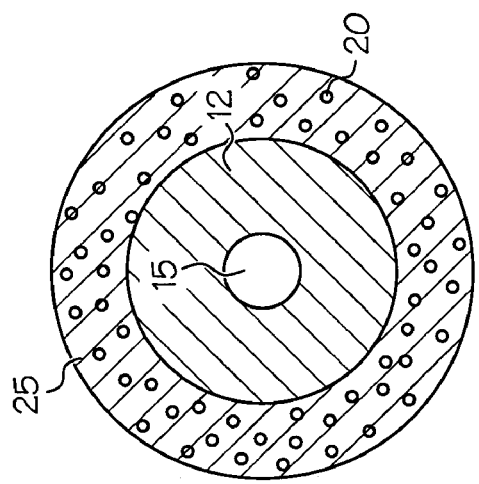

Conductivity-enhancing agent 20 may be associated with delivery element 10 in any manner such that introduction of at least a portion of the delivery element 10 to a tissue of a subject allows for the conductivity enhancing 20 agent to elute or dissolve into the tissue. FIGS. 1B–1E show examples of associations of conductivity-enhancing agent 20 with delivery element. FIG. 1B shows that conductivity enhancing agent 20 may be disposed in a body member 12 of delivery element 10. While FIG. 1B shows conductivity enhancement agents 20 disposed throughout the body member 12, the conductivity enhancement agents may be disposed within one or more portions of the body member 12 (not shown). FIG. 1C shows that conductivity-enhancing agent 20 may be disposed on the body member 12. If a given conductivity-enhancing agent 20 is disposed partially within the body member 12 or other layer and partially protrudes from a surface of the body member 12 or other layer, the conductivity-enhancing agent 20 is considered both disposed in and disposed on the body member 12 or other layer. Further, while not shown, it will be understood that conductivity-enhancing agents 20 may be both disposed in and disposed on the body member 12 of the delivery element 10. FIGS. 1D and 1E show embodiments where a coating layer 25 is disposed on the body member 12 and the conductivity-enhancing agent is disposed in (1D) or on (1E) the coating layer. As with the body member 12, conductivity-enhancing agent 20 may be disposed throughout the coating layer 12, in a portion of the coating layer 12, and/or both within and on the coating layer 12.

It will be understood that conductivity-enhancing agent 20 as depicted in FIGS. 1A–1E, other subsequent Figures, and throughout the present disclosure may refer to a plurality of different conductivity-enhancing agents 20. For example, a given conductivity-enhancing agent 20 depicted in FIG. 1A may be, e.g., NaCl and a different conductivity-enhancing agent 20 may be, e.g., $NaHCO_3$.

Figure 2A:
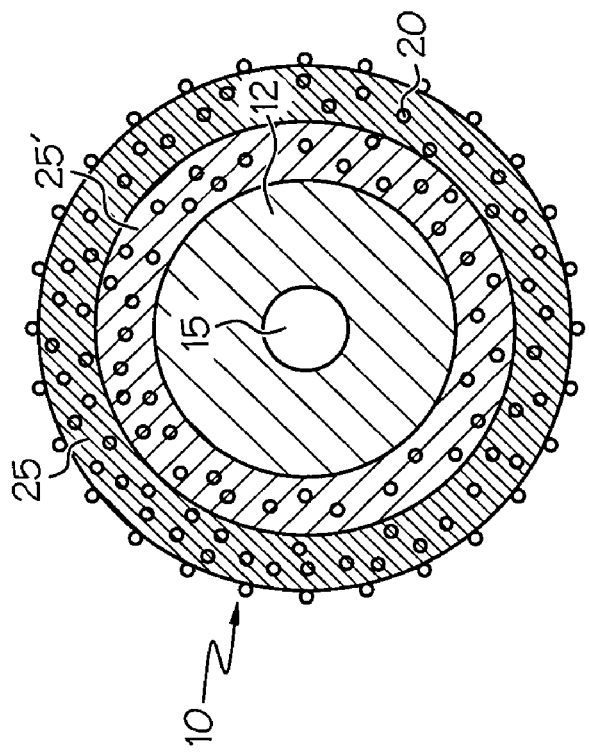
FIGS. 2A and 2B are diagrammatic illustrations of cross-sections of delivery elements showing varying concentrations of conductivity-enhancing agent disposed in and on more than one layer of delivery elements according to embodiments of the invention.
Figure 2B:
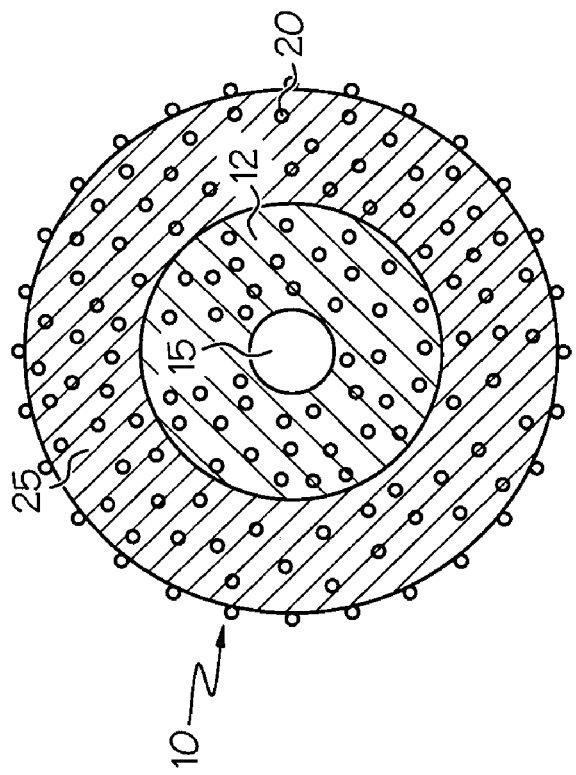

In various embodiments of the invention, conductivity-enhancing agents 20 are disposed on or in more than one layer of delivery element 10. For example, conductivity-enhancing agent 20 may be disposed on or in a body member 12 of delivery element and/or on or in one or more coating layer 25 of delivery element. FIG. 2A shows an embodiment where conductivity-enhancing agent 20 is disposed within or on body member 12 and within or on coating layer 25 of delivery element 10. FIG. 2B shows an embodiment where conductivity-enhancing agent 20 is disposed on or in a first coating layer 25 and on or in a second coating layer 25'. Of course, two, three, four, five, six, or more coating layers 25 may be disposed about body member 12 of delivery element 10 and conductivity enhancing agent 20 may be disposed in or on the body member 12 and/or none, some, or all of the one or more coating layers 25.

Figure 3B:
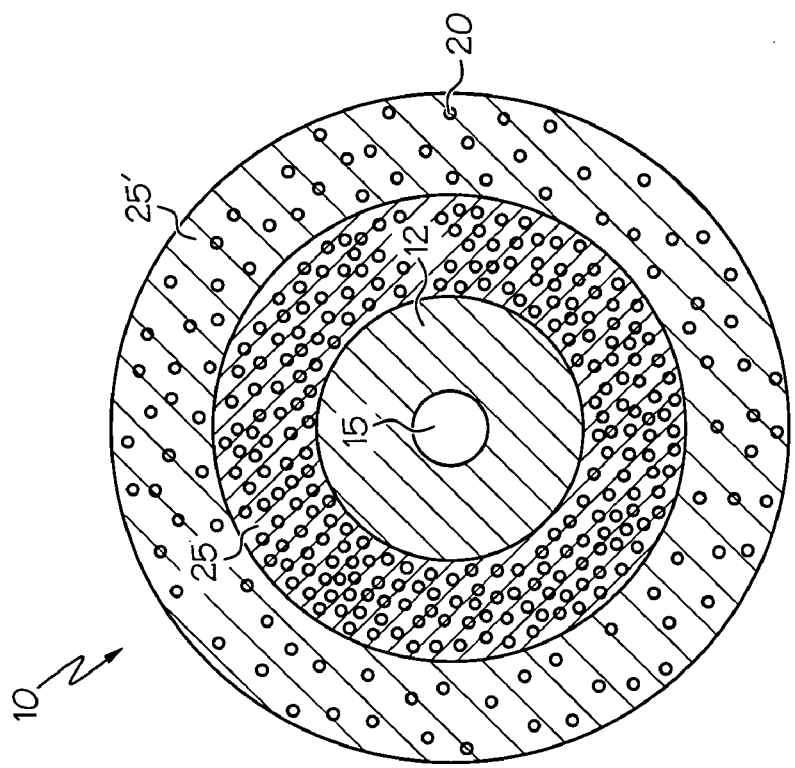
FIGS. 3A and 3B are diagrammatic illustrations of cross-sections of delivery elements showing varying concentrations of conductivity-enhancing agent disposed in and on layers of delivery elements according to embodiments of the invention.
Figure 3A:
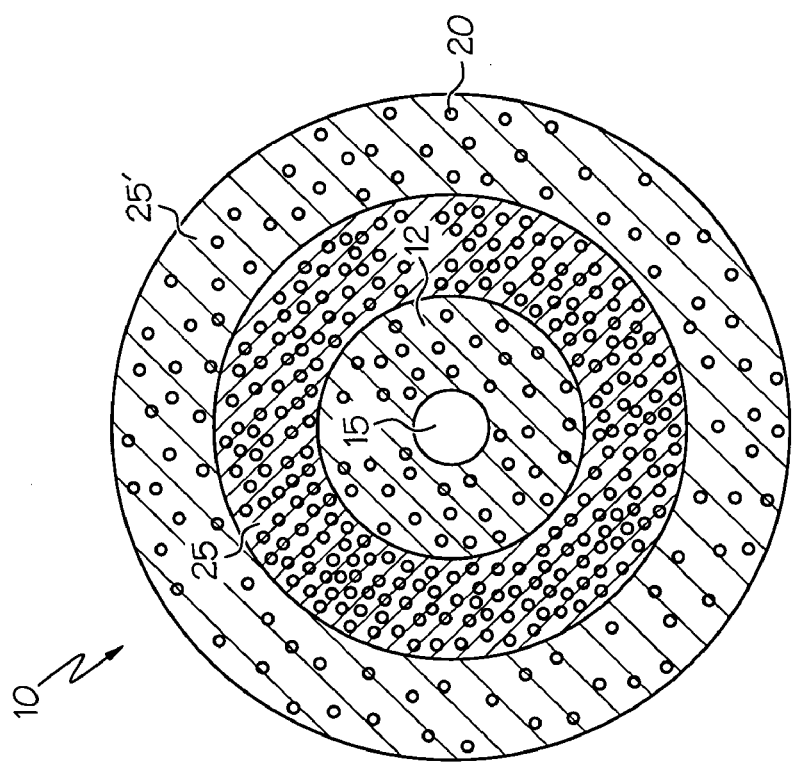

The concentration of conductivity-enhancing agents 20 within various layers (depicted as body member 12 or coating layer 25, 25') may be the same or different. Any concentration may be used. For example, conductivity-enhancing agent 20 may comprise about 0.1% to about 50%, or from about 1% to about 10%, of the weight of the layer. In some circumstances, it may be desirable to place a higher concentration of conductivity-enhancing agent 20 in one or more layers relative to other layers; e.g., when continued infusion of conductivity-enhancing agent 20 into body tissue over time or repeated insertions of delivery element 12 into tissue are desired. FIG. 3A shows a delivery element 10, where first coating layer 25 comprises a higher concentration of conductivity-enhancing agent 20 within or on intermediate coating layer 25 than in outer coating layer 25' or body member 12. In the embodiment illustrated by FIG. 3A, body member 12 is permeable to conductivity-enhancing agent 20 and conductivity-enhancing agent 20 may elute into lumen 15. Conductivity-enhancing agent 20 may also elute out of outer coating layer 25' into body tissue. Increased initial concentration of conductivity-enhancing agent 20 in intermediate coating layer 25 may effectively replenish the supply of conductivity-enhancing agent 20 in outer coating layer 25' and body member 12 such that conductivity-enhancing agent 20 may elute into lumen 15 or tissue. In the embodiment illustrated in FIG. 3B, body member 12 is essentially impermeable to conductivity-enhancing agent 20 and intermediate coating layer 25 comprises a higher concentration of conductivity-enhancing agent 20 that outer coating layer 25'. Conductivity-enhancing agent 20 in the intermediate coating layer may replenish supply in the outer coating layer 25' over time or during repeated insertion of delivery element 10 into tissue.

It should be understood that in certain embodiments of the invention, delivery element does not comprise a lumen 15.

Release profile of conductivity-enhancing agent 20 from delivery element 10, may be varied. As described above, location of conductivity-enhancing agent 20 in or on delivery element 10, as well as concentration of conductivity-enhancing agent 20 at a location, provides a means for achieving control over when conductivity-enhancing agent 20 is released. Release profile may be varied by controlling the nature of the conductivity-enhancing agent 20 to be released. For example, conductivity enhancing agents 20 having larger component sizes would be expected to elute more slowly from delivery element 10 than those having smaller component sizes. Thus, the extent to which a conductivity-enhancing salt is hydrated may affect the rate at which ions of the salt can elute out of delivery element. Further, the extent to which an ion associates with water may affect the rate at which the ion may elute out of delivery element 10 into tissue. Ions with larger charge densities may associate with more water molecules than ions with lesser charge densities and may elute more slowly. Additionally, ions having greater molecular mass may elute more slowly than ions having lesser molecular mass. Further, chemical gradients between chemical species within tissue into which delivery element 10 is inserted and chemical species within delivery element may affect the dynamic rate at which chemical species elute out of delivery element. With these and other considerations in mind, it may be desirable, in some circumstances, to vary the location of slower eluting conductivity-enhancing agents 20 and faster eluting conductivity enhancing agents 20 within or on delivery element 10.

For example, in situations, e.g. where the delivery element 10 may be inserted into tissue more than one time, it may be desirable to elute roughly the same amount of conductivity-enhancing agent 20 each time the delivery element 10 is inserted. One way to achieve substantially uniform release is to dispose a mixture of slower and faster eluting conductivity-enhancing agents 20 on or in therapy delivery element 10 such that a larger proportion of faster eluting agents 20 are introduced into tissue on the first insertion of delivery element into tissue, and increasing proportions of slower eluting agents 20 are introduced on subsequent insertions. Alternatively, a substantial amount of conductivity-enhancing agent 20, whether slow or fast eluting, may be incorporated into or on delivery element 10, such that during each use period, which may be relatively small compared to an exponential decay release profile, an approximately similar amount of conductivity-enhancing agent 20 is released over several uses, even with an exponential release profile. That is, the delivery element 10 may be loaded with a large reserve of conductivity-enhancing agent 20.

The rate at which conductivity-enhancing element 20 may be released from delivery element 10 into tissue may also be controlled by properties of coating layers 25 and/or body member 12, as well as the manner in which conductivity-enhancing agent 20 is disposed on or in coating layers 25 and/or body member.

Coating Layer

Coating layer 25 may be formed of any material capable of releasing one or more conductivity-enhancing agent 20 into tissue when placed in contact with the tissue. Preferably, coating layer 25 is acceptable for at least temporary use within a human body. Coating layer 25 is also preferably compatible with conductivity enhancing agent 20.

Examples of commonly used materials that may be used to form coating layers 25 include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE).

One or more coating layer 25 according to various embodiments of the invention may comprise a biodegradable polymeric material, such as synthetic or natural bioabsorbable polymers. Synthetic bioabsorbable polymeric materials that can be used to form the coating layers include poly (L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly (ether-esters) such as PEO/PLA, polyalkylene oxalates, and polyphosphazenes. According to another exemplary embodiment of the present invention, the polymeric materials can be natural bioabsorbable polymers such as, but not limited to, fibrin, fibrinogen, cellulose, starch, collagen, and hyaluronic acid.

Coating layers 25 may comprise polymeric materials designed to control the rate at which conductivity-enhancing agent is released, leached, or diffuses from the polymeric material. As used herein, "release", "leach", "diffuse", "elute" and the like are used interchangeably when referring to a conductivity-enhancing agent 20 with respect to a coating layer 25 or body member 12 of a delivery element. Any known or developed technology may be used to control the release rate. For example, a coating layer may be designed according to the teachings of WO/04026361, entitled "Controllable Drug Releasing Gradient Coating for Medical Devices."

Coating layer 25 of delivery element 10 may be in the form of a tube, sheath, sleeve, coating, or the like. Coating layer 25 may be extruded, molded, coated on body member 12, grafted onto body member 12, embedded within body member 12, adsorbed to body member 12, etc. Polymers of coating layers 25 may be porous or non-porous. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$ or by foaming the polymeric material prior to extrusion or coating.

Depending upon the type of materials used to form coating layers 25 of the present invention, the coatings can be applied to the surface of a body member 12 or underlying coating layer 25 through any coating processes known or developed in the art. One method includes directly bonding the coating material to a surface of body member 12 or underlying coating layer 25. By directly attaching a polymer coating to the body member 12 or underlying coating layer 25, covalent chemical bonding techniques may be utilized. Body member 12 or underlying coating layer 25 surface may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, and etching with strong organic solvents. Alternatively, the coating layer 25 may be indirectly bound to body member 12 or underlying coating layer 25 through intermolecular attractions such as ionic or Van der Waals forces.

Conductivity-enhancing agent 20 may be incorporated into a coating layer 25 in a variety of ways. For example, conductivity-enhancing agent 20 can be covalently grafted to a polymer of the coating layer 25, either alone or with a surface graft polymer. Alternatively, conductivity-enhancing agent 20 may be coated onto the surface of the polymer either alone or intermixed with an overcoating polymer. Conductivity-enhancing agent 20 may be physically blended with a polymer of a coating layer 25 as in a solid-solid solution. Conductivity-enhancing agent 20 may be impregnated into a polymer by swelling the polymer in a solution of the appropriate solvent. Any means of incorporating conductivity-enhancing agent 20 into or on a coating layer 25 may be used, provided that conductivity-enhancing agent 20 may be released, leached or diffuse from coating layer 25 on contact with bodily fluid or tissue.

A polymer of a coating layer 25 and a conductivity-enhancing agent 20 may be intimately mixed either by blending or using a solvent in which they are both soluble. This mixture can then be formed into the desired shape or coated onto an underlying structure of the medical device. One exemplary method includes adding one or more conductivity enhancing agents 20 to a solvated polymer to form a conductivity enhancing agent 20/polymer solution. The conductivity enhancing agent 20/polymer solution can then be applied directly to the surface of body member 12 or underlying coating layer 25; for example, by either spraying or dip coating delivery element 10. As the solvent dries or evaporates, the conductivity enhancing agent 20/polymer coating is deposited on delivery element 12. Furthermore, multiple applications can be used to ensure that the coating is generally uniform and a sufficient amount of conductivity enhancing agent 20 has been applied to delivery element 10.

Alternatively, an overcoating polymer, which may or may not be the same polymer that forms the primary polymer of body member 12 or underling coating layer 25, and conductivity-enhancing agent 20 are intimately mixed, either by blending or using a solvent in which they are both soluble, and coated onto body member 12 or underling coating layer 25. Any overcoating polymer may be used, as long as the polymer is able to bond (either chemically or physically) to the polymer of an underlying layer of delivery element 10.

In addition, a polymer of a coating layer 25 may be swelled with an appropriate solvent, allowing a conductivity-enhancing agent 20 to impregnate the polymer.

Conductivity-enhancing agent 20 may also be covalently grafted onto a polymer of a coating layer 25. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), may be used to initiate surface grafting.

Body Member

Body member 12 of delivery element 10 may be made of any material onto or into which a conductivity-enhancing agent may be disposed or onto or into which a coating layer comprising a conductivity-enhancing element may be directly or indirectly disposed, such that the conductivity-enhancing element may be released into tissue or bodily fluid when delivery element is contacted with the tissue or fluid. Preferably, body member 12 is formed of material acceptable for at least temporary use within a human body.

In an embodiment of the invention, delivery element 10 is a needle electrode 30 of a tissue ablation device 100, as shown in, e.g., FIGS. 6–9. Body member 12 of needle electrode 30 may be made of any electrically conductive material. For example, body member 12 of needle electrode may be formed of a metallic material such as, but not limited to, aluminum, 316L stainless steel, MP35N alloy, superelastic Nitinol nickel-titanium, titanium alloys, and other alloys such as a wrought Cobalt-Chromium-Nickel-Molybdenum-iron alloy. Needle electrode 30 may take the form of a Nitinol needle electrode as used in Medtronic's Precision™ Plus TUNA system.

Needle electrode 30 may be treated by, e.g., ionization, heating, photochemical activation, oxidizing acids, sintering, physical vapor deposition, chemical vapor deposition and/or etching with strong organic solvents, as discussed above, to facilitate disposing conductivity-enhancing agent 20 directly on the needle electrode 30.

One or more coating layers, one or more of which may comprise a conductivity-enhancing agent 20, may be disposed on a needle electrode according to the teachings of the invention. The needle electrode 30 may optionally be treated as discussed above to facilitate coating of a polymeric material onto the needle electrode 30. Alternatively, a coating layer 25 in the form of a sheath, sleeve, or the like is disposed about a needle electrode 30. The sheath, sleeve, etc. may be disposable or designed for one use. Preferably, coating layers 25 disposed on or about a needle electrode 30 do not substantially interfere with the conductive properties of the needle electrode 30. In particular, it is desirable that the needle electrode 30 comprising a coating layer 25 remain conductive to high frequency energy, such as RF energy. Use of a porous polymer as a coating layer 25 and/or use of a thin coating layer 25 are but a few examples of how conductivity of a needle electrode 35 may be maintained. A thin coating layer may be, for example, less than about 10,000 μm thick, less than about 200 μm thick, less than about 30 μm thick, in the range of about 10 μm to about 10,000 μm, or about 20 μm to about 200 μm thick, or about 10 μm to 30 μm thick. Due to heat generation associated with application of energy to the needle electrode, it may be desirable in certain circumstances that the coating layer 25 be formed of a thermostable material. However, it may also be desirable that the coating layer 25 be thermo-unstable, particularly when the coating layer consists of material, which may be readily acceptably to a human tissue, such as bioresorable polymers. The bioresporbable polymer may break down or disintegrate upon application of energy to the needle electrode 30, releasing substantially all of the conductivity-enhancing agent 20 disposed on or in the polymer.

Figure 4:
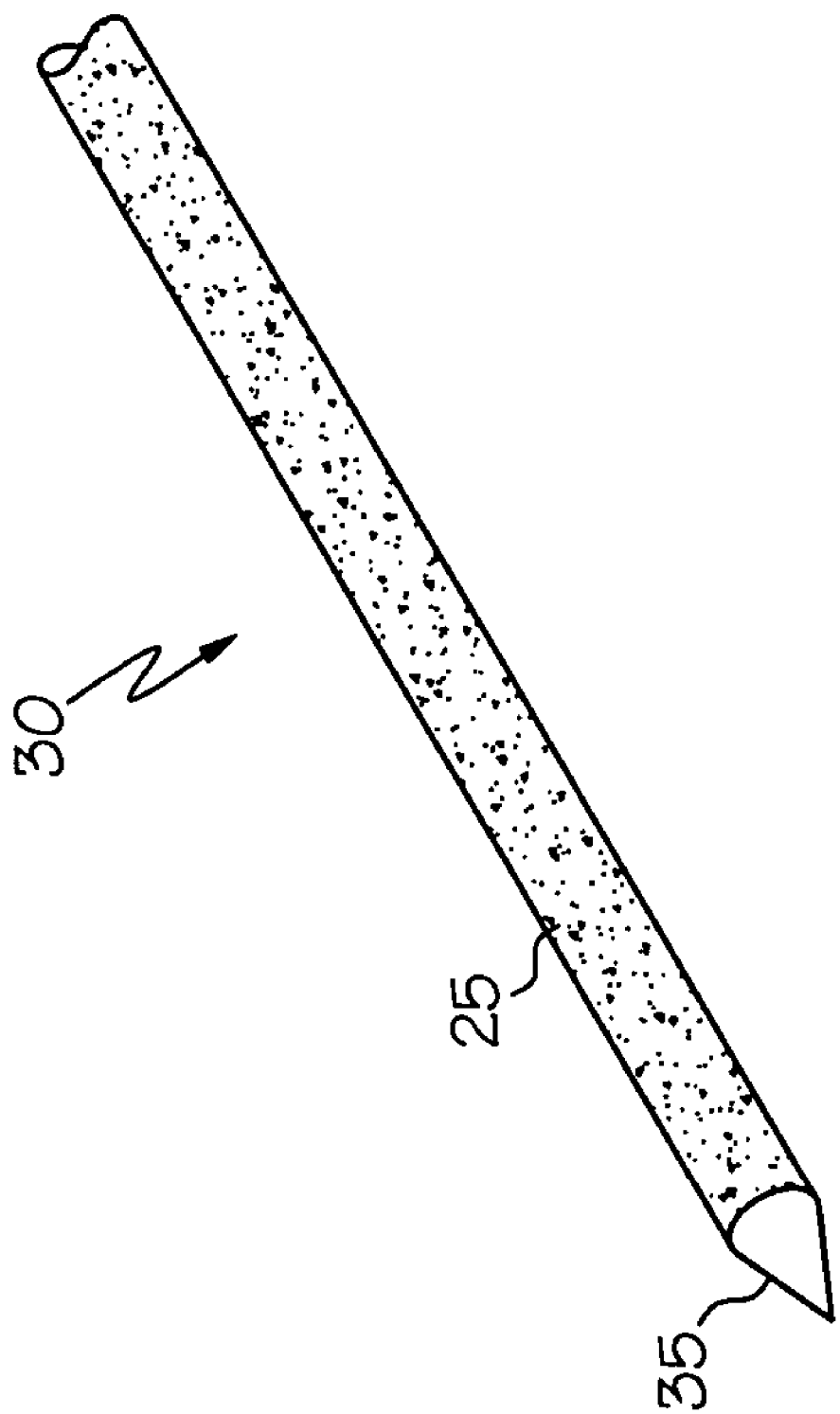
FIG. 4 is a diagrammatic representation of a needle electrode coated with a porous polymer according to an embodiment of the invention.

An exemplary embodiment of a needle electrode comprising a coating layer 25 comprising a conductivity enhancing agent is depicted in FIG. 4. The needle electrode 30 comprises a tapered end portion 35 adapted to be inserted into tissue. The coating layer 25 is coated directly onto the surface of the needle electrode 30. The coating layer 25 comprises a porous polymer.

Another exemplary embodiment of a needle electrode according to the invention is depicted in FIG. 5. The needle electrode 30 comprises a tapered end portion 35 adapted to be inserted into tissue. A coating layer 25 in the form of a sheath is disposed about the needle electrode 30. The coating layer 25 comprises a porous polymer.

In an embodiment, delivery element 10 is an insulating sheath 40 of a tissue ablation device 100, as shown in, e.g., FIGS. 6–9. Body member 12 of sheath 40 may be made of any electrically insulating material. Examples of suitable materials include those discussed above with regard to coating layers 25. Typically, coating layer 25 will comprise silicone or polyurethane. Conductivity-enhancing agents 20 may be incorporated into body member 12 of insulating sheath 40 as described above with regard to coating layers 25. One or more coating layers 25, one or more of which may comprise one or more conductivity enhancing agents 20, may be disposed on or about insulating sheath 40.

In alternative embodiments not shown, delivery element 10 may be a jacket adapted to be disposed between a sheath 40 and a needle electrode 30 of a tissue ablation device 100 or may be an element adapted to be delivered to a tissue along with a needle electrode of a tissue ablation device.

Tissue Ablation Device

An embodiment of the invention provides a tissue ablation device 100. FIG. 6 shows an external view of a tissue ablation device 100 according to an embodiment of the invention. As shown in FIG. 6, the tissue ablation device 100 comprises a housing 110 and an elongate probe member 120 extending from the housing 110. The elongate probe member 120 has a proximal end 130 and a distal end 140 and comprises one or more passageways 150 extending at least substantially between the proximal end 130 and the distal end 140. The tissue ablation device further comprises an actuator, a portion of which is shown in the form of a trigger extending from a handle 125 in the embodiment depicted in FIG. 6.

The device further comprises a needle electrode 30 having an exterior surface and a proximal portion and a distal portion. As shown in FIG. 7, which is a cross section of the device shown in FIG. 6 at line 180, the needle electrode 30 is slidably mounted in a passageway 150 of the elongate probe member 130. An insulating sheath 40 may also be slidably mounted in the passageway 150 such that the needle 30 is slidably mounted in a lumen 170 of the sheath 40. As shown in FIGS. 8a–9b, where FIGS. 8a and 9a are longitudinal sections of the device 100 to the left of line 180 in FIG. 6 and FIGS. 8b and 9b are longitudinal sections of the device 100 to the left of line 180 in FIG. 6, the actuator is adapted to cause the distal portion of the needle 30 to extend into a target tissue location.

Referring to FIGS. 8a and 8b, the needle electrode 30 of the tissue ablation device 100 is retracted (i.e., the distal portion of the needle 30 is within the confines of the passageway 150), and the actuator 160 is disengaged. FIGS. 9a and 9b show the actuator engaged and the needle electrode 30 deployed (i.e, extending through the passageway 150). Also shown in FIGS. 8a–9b, the acutator may also be coupled to the insulating sheath 40 and be adapted to cause the distal portion of the insulating sheath 40 to extend into a target tissue location. The insulating sheath 40 may be retracted (not shown) prior to applying ablative energy to the tissue location via the needle electrode. The needle electrode 40 may be coupled to an energy generator (not shown), such as an RF generator, such that ablative energy may be applied to the tissue through the needle 30.

As discussed above, at least one of the needle electrode 30, the insulating sheath 40, or another element is a delivery element 10 associated with a conductivity-enhancing agent 20. If a delivery element 10 is an element other than a needle electrode 30 or insulating sheath 40, it is preferred that the other element (not shown) is coupled to the actuator 160 and that the actuator is adapted to cause a distal portion of the other element to extend into the target tissue location. When the delivery element 10 is the needle electrode 30, insulative sheath 40, or other element in proximity to needle electrode 30, a subablation pulse may be applied to the needle electrode to drive conductivity-enhancing agent 20 into the tissue location prior to delivering ablative energy. In addition, it is preferred that delivery element(s) 10 are deployed in the tissue location for sufficient time to allow conductivity-enhancing agent 20 to elute into the tissue location.

The device 100 depicted in FIGS. 6–9 is of course simplified for illustrative purposes. More details as to how a tissue ablation device 100, device components, and systems according to various embodiments of the invention may be constructed and used can be found in, e.g., U.S. Pat. No. 5,964,756. An exemplary device 100 and system that may be modified according the teachings of the present invention is Medtronic's Precision™ Plus TUNA System. The Precision™ Plus TUNA System, devices, and components thereof, as well as associated Medtronic brochures and user guides, are hereby incorporated herein by reference.

Devices 100 comprising delivery elements 10 according to the teachings of the invention may be used to ablate any tissue in a subject, such as a human patient, in need thereof. For example, prostate tissue may be ablated, tumors may be ablated, cardiac tissue may be ablated, etc. Accordingly, various diseases or disorders may be treated using a device 100 comprising a delivery element 10 according to the teachings of the invention. In general, any disease or disorder of a subject that may benefit from ablation of a tissue may be treated. For example, hyperplasia, such as benign prostatic hyperplasia, or cancer may be treated.

Various embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system comprising:
    an ablation needle electrode, comprising:
    an electrically conductive body member having an exterior surface and a tapered end portion adapted to be inserted into tissue; and
    a coating layer disposed on at least a portion of the exterior surface of the body member, the coating layer comprising a conductivity-enhancing agent,
    wherein the conductivity-enhancing agent is capable of being released into a body tissue when the needle electrode is in contact with the body tissue; and
    a radio frequency generator configured to be connected to the ablation needle to provide ablative energy to the tissue.

2. The system of claim 1, wherein the body member comprises a metal or metal alloy.

3. The system of claim 2, wherein the metal alloy is a nickel-titanium alloy.

4. The system of claim 2, wherein the nickel-titanium alloy is Nitinol.

5. The system of claim 1, wherein the coating layer comprises a polymer.

6. The system of claim 5, wherein the polymer is selected from the group consisting of polyurethane, polyester, polyether, polysulfone, polyphenyleneoxide, and polytetrafluoroethylene (PTFE).

7. The system of claim 5, wherein the needle electrode is capable of transmitting energy to a body tissue.

8. The system of claim 7, wherein the polymer is a non-porous polymer having a thickness less than about 200 µm.

9. The system of claim 8, wherein the thickness is less than about 30 µm.

10. The system of claim 8, wherein the thickness is in the range of about 10 µm to about 30 µm.

11. The method of claim 7, wherein the polymer is a thermostable polymer.

12. The method of claim 7, wherein the polymer is a bioresorbable polymer.

13. The system of claim 1, wherein the conductivity-enhancing agent is a salt.

14. The system of claim 13, wherein the salt comprises sodium, potassium, calcium, or magnesium.

15. The system of claim 13, wherein the salt comprises nitrate, nitrite, sulfate, phosphate, or carbonate.

16. The system of claim 15, wherein the salt comprises sodium, potassium, calcium, or magnesium.

17. The system of claim 13, wherein the salt is selected from the group consisting of NaCl, $CaCl_2$, $MgCl_3$, $KMgCl_3$, $Na_2SO_3$, $CaSO_4$, $MgSO_4$, $Na_2HPO_4$, $Ca_{10}(PO_4)_6$, $Mg_3(PO_4)_2$, $NaHCO_3$, $CaCO_3$, $MgCO_3$, $NaNO_3$, $NaNO_2$, KCl, $KNO_3$, $KNO_2$, and $CaMgCO_3$.

18. The system of claim 1, wherein the conductivity-enhancing agent comprises between about 0.1% and about 50% by weight of the coating layer.

19. The system of claim 18, wherein conductivity-enhancing agent comprises between about 1% and about 10% by weight of the coating layer.

20. The system of claim 5, wherein the conductivity-enhancing agent comprises between about 0.1% and about 50% by weight of the coating layer.

21. A device for ablating tissue at a target location, comprising:
   a housing;
   an elongate probe member
      extending from the housing,
      having proximal and distal ends, and
      being provided with one or more passageways extending at least substantially between the proximal end and the distal end;
   a needle electrode
      comprising an electrically conductive body member having an exterior surface, a proximal portion and a distal portion,
      further comprising a conductivity-enhancing agent disposed on at least a portion of the exterior surface of the body member, and
      being slidably mounted within one of the one or more passageways of the elongate probe member; and
   an actuator
      coupled to the proximal portion of the needle electrode and adapted to cause the distal portion of the needle electrode to extend into the target location,
   wherein the conductivity-enhancing agent is capable of being released into tissue at the target location when the needle electrode is extended into the target location.

22. The device of claim 21, further comprising a sheath
   having proximal and distal portions,
   having a lumen extending at least substantially between the proximal and distal portions of the sheath, and
   being slidably mounted within the same passageway as the needle electrode,
   wherein the needle electrode is slidably mounted within the lumen of the sheath.

23. The device of claim 22, wherein the actuator is coupled to the proximal portion of the sheath and adapted to cause the distal portion of the sheath to extend into the target location.

24. The device of claim 23, wherein the sheath comprises a body member and a conductivity-enhancing agent disposed in or on the body member; the conductivity-enhancing agent capable of being released into tissue at the sheath is extended into the target location.

25. The device of claim 23, wherein the sheath comprises a body member, a coating layer, and a conductivity-enhancing agent capable of being released into tissue at the target location when the sheath is extended into the target location, wherein the conductivity-enhancing agent is disposed in or on at least one of the body member or the coating layer.

26. A device for ablating tissue at a target location, comprising:
   a housing;
   an elongate probe member
      extending from the housing,
      having proximal and distal ends, and
      being provided with one or more passageways extending at least substantially between the proximal end and the distal end;
   a needle electrode
      comprising an electrically conductive body member having an exterior surface, a proximal portion and a distal portion,
      further comprising a coating layer disposed on at least a portion of the exterior surface of the body member, the coating layer comprising a conductivity-enhancing agent, and
      being slidably mounted within one of the one or more passageways of the elongate probe member; and
   an actuator
      coupled to the proximal portion of the needle electrode and adapted to cause the distal portion of the needle electrode to extend into the target location,
   wherein the conductivity-enhancing agent is capable of being released into tissue at the target location when the needle electrode is extended into the target location.

27. The device of claim 26, further comprising a sheath
   having proximal and distal portions,
   having a lumen extending at least substantially between the proximal and distal portions of the sheath, and
   being slidably mounted within the same passageway as the needle electrode,
   wherein the needle electrode is slidably mounted within the lumen of the sheath.

28. The device of claim 27, wherein the actuator is coupled to the proximal portion of the sheath and adapted to cause the distal portion of the sheath to extend into the target location.

29. The device of claim 28, wherein the sheath comprises a body member and a conductivity-enhancing agent disposed in or on the body member; the conductivity-enhancing agent capable of being released into tissue at the target location when the sheath is extended into the target location.

30. The device of claim 28, wherein the sheath comprises a body member, a coating layer, and a conductivity-enhancing agent capable of being released into tissue at the target location when the sheath is extended into the target location,
   wherein the conductivity-enhancing agent is disposed in or on at least one of the body member or the coating layer.

31. A device for ablating tissue at a target location, comprising:
   a housing;
   an elongate probe member
      extending from the housing,
      having proximal and distal ends, and
      being provided with one or more passageways extending at least substantially between the proximal end and the distal end;

a needle electrode
- comprising an electrically conductive body member having an exterior surface, a proximal portion and a distal portion, and
- being slidably mounted within one of the one or more passageways of the elongate probe member;

a delivery element
- comprising a body member and a conductivity-enhancing agent disposed on or in the delivery element body member,
- having a proximal portion and a distal portion, and
- being slidably mounted in a passageway of the elongate probe member; and an actuator
- coupled to the proximal portion of the needle electrode and adapted to cause the distal portion of the needle electrode to extend into the target location, and
- coupled to the proximal portion of the delivery element and adapted to cause the distal portion of the delivery element to extend into the target location, wherein the conductivity-enhancing agent is capable of being released into tissue at the target location when the delivery element is extended into the target location.

32. A device for ablating tissue at a target location, comprising:

a housing;

an elongate probe member
- extending from the housing,
- having proximal and distal ends, and
- being provided with one or more passageways extending at least substantially between the proximal end and the distal end;

a needle electrode
- comprising an electrically conductive body member having an exterior surface, a proximal portion and a distal portion, and
- being slidably mounted within one of the one or more passageways of the elongate probe member;

a delivery element
- comprising a body member, a coating layer and a conductivity-enhancing agent disposed on or in at least one of the delivery element body member or delivery element coating layer,
- having a proximal portion and a distal portion, and
- being slidably mounted in a passageway of the elongate probe member; and an actuator
- coupled to the proximal portion of the needle electrode and adapted to cause the distal portion of the needle electrode to extend into the target location, and
- coupled to the proximal portion of the delivery element and adapted to cause the distal portion of the delivery element to extend into the target location, wherein the conductivity-enhancing agent is capable of being released into tissue at the target location when the delivery element is extended into the target location.

33. A method for ablating tissue at a target location, comprising:
- introducing into the target location a delivery element comprising a conductivity-enhancing agent, the conductivity-enhancing agent capable of increasing conductivity of the tissue when dissolved in the target location;
- introducing an electrode into the target location; and
- ablating the tissue by applying energy to the target location via the electrode.

34. The method of claim 33, wherein the electrode is the delivery element, and introducing the delivery element and introducing the electrode comprises introducing the electrode.

35. The method of claim 34, further comprising applying a sub-ablation amount of energy to drive the conductivity-enhancing agent into the tissue.

36. The method of claim 33, wherein introducing the delivery element comprises introducing a sheath comprising the conductivity-enhancing agent.

37. The method of claim 36, further comprising applying a sub-ablation amount of energy to drive the salt into the tissue.

38. The method of claim 37, further comprising retracting the sheath prior to ablating the tissue.

39. The method of claim 36, further comprising retracting the sheath prior to ablating the tissue.

* * * * *